(12) United States Patent
Mason (10) Patent No.: US 7,677,296 B2
(45) Date of Patent: Mar. 16, 2010

(54) PRECISION CAST DENTAL INSTRUMENT

(75) Inventor: Robert M. Mason, Tallahassee, FL (US)

(73) Assignee: Cloudland Institute LLC, Lookout Mountain, GA (US)

(*) Notice: Subject to any disclaimer, the term of this patent is extended or adjusted under 35 U.S.C. 154(b) by 312 days.

(21) Appl. No.: 11/726,905

(22) Filed: Mar. 23, 2007

(65) Prior Publication Data

US 2007/0184406 A1    Aug. 9, 2007

Related U.S. Application Data

(63) Continuation of application No. 10/654,260, filed on Sep. 3, 2003, now abandoned.

(60) Provisional application No. 60/408,584, filed on Sep. 6, 2002.

(51) Int. Cl.
*B22D 30/00* (2006.01)
*A61C 5/02* (2006.01)

(52) U.S. Cl. ..................... 164/122; 29/896.1

(58) Field of Classification Search ............... 164/122, 164/122.1, 125; 29/896.1, 896.11
See application file for complete search history.

(56) References Cited

U.S. PATENT DOCUMENTS

| | | | |
|---|---|---|---|
| 717,594 | A | 1/1903 | Miles, Jr. |
| 1,022,838 | A | 4/1912 | Funk |
| 3,871,836 | A * | 3/1975 | Polk et al. ............... 428/656 |
| 4,708,653 | A | 11/1987 | Eichen et al. |
| 5,066,230 | A | 11/1991 | Weissman |
| 5,299,937 | A | 4/1994 | Gow |
| 5,735,689 | A | 4/1998 | McSpadden |
| 5,882,198 | A | 3/1999 | Taylor et al. |
| 5,984,996 | A | 11/1999 | Gonsalves et al. |
| 6,213,771 | B1 | 4/2001 | Fischer |
| 6,234,796 | B1 | 5/2001 | Braun |
| 6,409,506 | B1 | 6/2002 | Graybill |
| 6,431,863 | B1 * | 8/2002 | Sachdeva et al. ........... 433/102 |
| 6,641,395 | B2 * | 11/2003 | Kumar et al. ............. 433/165 |
| 2003/0126802 | A1 | 7/2003 | Rosenflanz |

* cited by examiner

*Primary Examiner*—Kevin P Kerns
(74) *Attorney, Agent, or Firm*—Luedeka, Neely & Graham, PC (57) ABSTRACT

An endodontic file (200) is provided particularly adapted for the removal of tooth structure, decayed or damaged nerve tissues or dentine material on the interior walls of a root canal or dentine and/or enamel from the external tooth wall. The endodontic instrument includes a shaft (202) having a shank portion (204) and a generally elongated working portion (206). The working portion preferably includes cutting or abrading features (232) adapted upon rotation and/or reciprocation of the instrument to cut, abrade or remove tissue from the interior walls of a root canal or dentine and/or enamel from the external tooth wall. The working portion extends from a proximal end (207) adjacent the shank portion to a distal end (208) terminating at a tip (250). The entire instrument and/or at least the working portion thereof is formed of an amorphous or essentially amorphous material having no or essentially no detectable crystalline structure and/or from a nanocrystalline material having an average crystalline grain size less than about 1 μm. The instrument may be formed by conventional grinding operations or by direct casting, forging or molding, in a manner producing an integral as-molded instrument having one or more sharp cutting edges. The instrument is inexpensive to manufacture and exhibits improved cutting-edge sharpness, wear resistance, lubriciousness and resistance to breakage.

5 Claims, 6 Drawing Sheets

PRECISION CAST DENTAL INSTRUMENT

RELATED APPLICATIONS

This application is a continuation of U.S. patent application Ser. No. 10/654,260, filed Sep. 3, 2003, now abandoned, which claims priority under 35 U.S.C. § 119(e) to U.S. provisional application Ser. No. 60/408,584, filed Sep. 6, 2002, now expired.

BACKGROUND OF THE INVENTION

1. Field of the Invention

The present invention relates generally to the field of dentistry and more particularly to rotating or oscillating cutting instruments and tools useful for the removal of tooth structure, including decayed or damaged nerve tissues and dentine material on the interior walls of the root canal and dentine and enamel from the external tooth wall.

2. Description of the Related Art

In the field of endodontics, one of the most important and delicate procedures is that of cleaning or extirpating a root canal to provide a properly dimensioned cavity while essentially maintaining the central axis of the canal. This step is important in order to enable complete filling of the canal without any voids and in a manner which prevents the entrapment of noxious tissue in the canal as the canal is being filled.

In a root canal procedure, the dentist removes injured tissue and debris from the canal prior to filling the canal with an inert filling material. In performing this procedure the dentist must gain access to the entire canal, shaping it as necessary. But root canals normally are very small in diameter, and they are usually quite curved. It is therefore very difficult to gain access to the full length of a root canal.

Many tools have been designed to perform the difficult task of cleaning and shaping root canals. Historically, dentists have used a wide multitude of tools to remove the soft and hard tissues of the root canal. These tools, usually called endodontic files, have been made by three basic processes. In one process, a file is created by twisting a prismatic rod of either square or triangular cross section in order to create a file with helical cutting/abrading edges ("K-file"). The second process involves grinding helical flutes into a circular or tapered rod to create a file with one or more helical cutting edges ("Hedstrom file"). The third method involves "hacking" or rapidly striking a circular or tapered rod with a blade at a given angle along the length of the rod, thus creating an endodontic file characterized by a plurality of burr-like barbs or cutting edge projections ("barbed file" or "broach"). Each of these methods produces an instrument having unique attributes, advantages, and disadvantages.

Endodontic files have historically been made from medical-grade stainless steels. But steel is inherently stiff and brittle and, thus, these tools can sometimes pose a significant danger of breakage in the curved root canal, particularly if over-torqued or fatigued. Modern endodontic instruments are often formed from exotic alloys such as nickel-titanium commonly known as "Nitinol™" or "NiTi." A series of comparative tests of instruments made of nickel-titanium alloy and stainless steel were conducted and published in an article entitled "An Initial Investigation of the Bending and the Torsional Properties of Nitinol Root Canal Files," Journal of Endodontics, Volume 14, No. 7, July 1988, pages 346-351. The reported tests demonstrated that the NiTi instruments exhibited superior flexibility and torsional properties as compared to stainless steel instruments.

Based on the initial success of these and similar studies, NiTi endodontic instruments have been commercially introduced and have become widely accepted in the industry. As the use of such NiTi instruments has proliferated, however, certain drawbacks have become apparent. One particularly well-documented drawback is the expense and difficulty of machining endodontic files from NiTi alloy. Slow grinding with fine-grit grinding wheels is the presently accepted method for machining NiTi alloys. But, even then, special procedures and parameters must typically be observed to reliably obtain clinically acceptable instruments. See, for example, U.S. Pat. No. 5,464,362 to Heath et. al., which describes a method of slow grinding a rod of a nickel-titanium alloy to create a fluted endodontic file. The cost of purchasing and operating the required specialized 6-axis grinding machines and other grinding/machining equipment and the time consumption of the grinding process itself make endodontic files produced by this method inordinately expensive when compared to their stainless steel counterparts.

Another significant drawback is the extreme tendency of the NiTi material to form latent burrs, rolled metal deposits and/or other imperfections along the desired cutting edges during the machining process. If these imperfections are not carefully monitored and controlled, they can have deleterious effects on file performance. Another significant drawback is that the cutting edges of presently available NiTi instruments are not as sharp as their stainless steel counterparts and tend to lose their sharpness more rapidly with use. Another significant drawback is reduced manipulation control due to reduced stiffness (excessive "rubberiness") and extreme torsional flexibility of presently available NiTi endodontic files as compared with stainless steel files. Another drawback is increased heat generation created by bare or oxidized NiTi surfaces rubbing against root canal walls.

These and other drawbacks have limited the growth of NiTi instruments and have created demand for improved manufacturing methods, alloys and instruments that overcome the aforenoted drawbacks.

SUMMARY OF THE INVENTION

The present invention provides an improved class of alloys and precision manufacturing techniques particularly suited and adapted for forming endodontic files, reamers, drills and similar cutting instruments having improved lubriciousness and resistance to wear and breakage.

In one preferred embodiment, the invention provides an endodontic file fabricated from one or more amorphous metal alloys. Such instruments exhibit greatly improved cutting-edge sharpness, wear resistance, lubriciousness and resistance to breakage from the propagation of cracks caused by crystalline defects.

In another preferred embodiment, the invention provides an endodontic instrument fabricated by direct casting, forging or molding. Most preferably, the endodontic instrument is fabricated as a single integral unit, including the working or cutting portion and the handle or attachment end thereof, from an amorphous metal alloy. Commercial quantities of such instruments can be quickly and economically manufactured using modified metal injection molding and/or amorphous metal die-casting techniques.

In another preferred embodiment, the invention provides an endodontic file fabricated from a bulk amorphous or nanocrystalline alloy material. The alloy material is preferably selected to have a relatively high ultimate tensile strength and a relatively low modulus of elasticity. The endodontic file is preferably formed by forcing an amorphous alloy under pressure into a suitably designed mold or die to form a cast integral body having one or more helical or non-helical flute patterns, cutting edges and/or any number of other desired working surface features. The endodontic file constructed in accordance with the invention possesses sharper and cleaner cutting edges than heretofore achieved using conventional grinding processes and is further capable of receiving an increased range of desired working surface features, such as cutting edges, barbs, projections, recesses and the like. The endodontic file constructed from amorphous alloy in accordance with the invention is also sharper, more lubricous and resistant to wear and breakage than instruments manufactured from conventional crystalline alloys.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and its essential features and advantages, certain preferred embodiments and modifications thereof will become apparent to those skilled in the art from the detailed description herein having reference to the figures that follow, of which.

DESCRIPTION OF THE PREFERRED EMBODIMENTS

Figure 1:
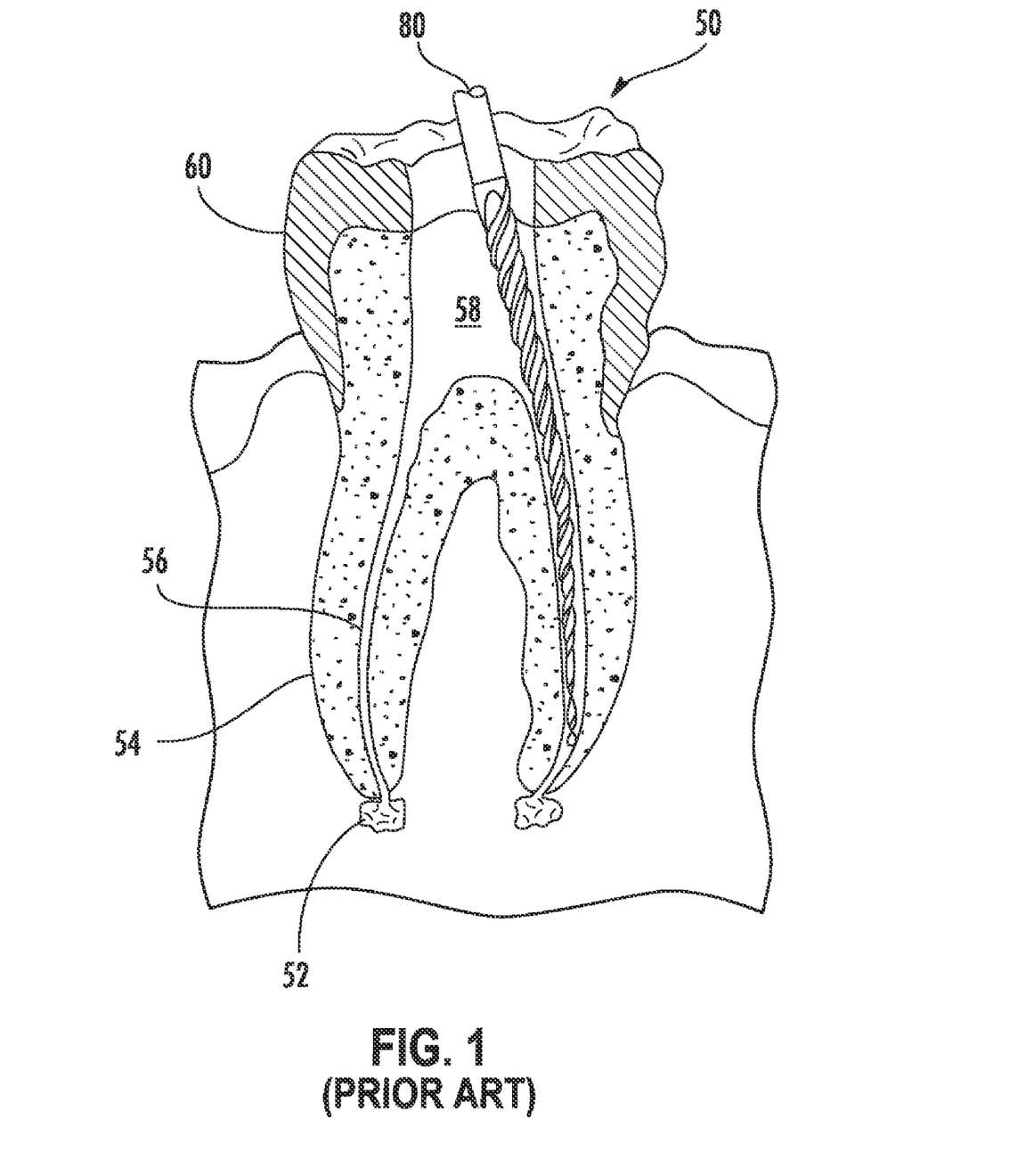
FIG. 1 is a section view of a tooth and associated root structure illustrating the use of an endodontic file for performing a typical root canal procedure.

FIG. 1 is a partial cross section of a tooth 50 and supporting root structure illustrating the use of a typical fluted endodontic file 80 to carry out a standard root canal procedure. The root canal 56 of a tooth houses the circulatory and neural systems of the tooth. These enter the tooth at the terminus 52 of each of its roots 54 and extend through a narrow, tapered canal system to a pulp chamber 58 adjacent the crown portion 60 of the tooth. If this pulp tissue becomes diseased or injured, it can cause severe pain and trauma to the tooth, sometimes necessitating extraction of the tooth. Root canal therapy involves removing the diseased tissue from the canal 56 and sealing the canal system in its entirety. If successful, root canal therapy can effectively alleviate the pain and trauma associated with the tooth so that it need not be extracted.

To perform a root canal procedure, the endodontist first drills into the tooth 50 to locate the root canal(s) 56 and then uses an endodontic file or reamer instrument 80 to remove the decayed, injured or dead tissue from the canal. These instruments are typically elongated cutting or abrading instruments which are rotated and/or reciprocated within the root canal either by hand or using a slow speed drill. The primary goal is to remove all of the decayed or injured pulp tissue while leaving the integrity of the central axis of the root canal relatively unaffected. Proper cleaning and shaping of the root canal 56 is important in order to allow complete filling of the root canal void in a homogenous three dimensional manner such that leakage or communication between the root canal system and the surrounding and supporting tissues of the tooth 50 is prevented. Once as much of the diseased material as practicable is removed from the root canal, the canal 56 is sealed closed, typically by reciprocating and/or rotating a condenser instrument in the canal to urge a sealing material such as gutta-percha into the canal.

One of the primary challenges in performing root canal therapy is that the root canals are not necessarily straight and are often curved or convoluted. Therefore, it is often difficult to clean the canal while preserving its natural shape. Many instruments (particularly the older, stainless steel instruments) have a tendency to straighten out the canal or to proceed straight into the root canal wall, altering the natural shape of the canal. In some extreme cases, the instrument may transport completely through the canal wall causing additional trauma to the tooth and/or surrounding tissues. Also, the openings of many root canals are small, particularly in older patients, due to calcified deposits on the root canal inner walls. Thus the files or reamers must be able to withstand the torsional load necessary to penetrate and enlarge the canal opening without breaking the instrument, as may also occasionally occur with the older stainless steel endodontic files.

To alleviate the transportation and breakage problems, highly flexible endodontic files fabricated from nickel-titanium alloy (Nitinol™ or NiTi) were introduced and have become widely accepted. See, e.g. U.S. Pat. No. 5,882,198, incorporated herein by reference. But conventional fluted instrument designs are difficult to manufacture from Nitinol alloys, often requiring expensive grinding operations and specialized 6-axis grinding machines to create the desired continuous helical fluting and sharp cutting edges.

FIGS. 2A-H are various views of a typical fluted endodontic file fabricated from a NiTi alloy. See, e.g. U.S. Pat. No. 5,882,198, incorporated herein by reference. The file 100 generally comprises a shaft 102 having a shank portion 104 and an elongated working portion 106. The working portion 106 extends from a proximal end 107 adjacent the base of the shank 104 to a distal end 108 terminating in a chisel tip 150. Typically, the shank portion 104 is securely gripped or otherwise permanently secured to a formed plastic or metal fitting or handle portion 109 for mating with the chuck of a dental handpiece (not shown). The fitting portion 109 includes a generally I-shaped flat side 182 which defines a step 184 and a generally semicircular disk 186 above and adjacent to a generally semi-circular groove 188. Such fitting 109 is typical of those employed in the dental industry for connecting or interfacing a dental tool with dental drill or handpiece.

Alternatively and/or in addition to the fitting portion 109, the shank portion 104 may include a knurled or otherwise treated surface (not shown) or plastic or metal handle to facilitate hand manipulation of the file 100. Thus, the instrument 100 may either be used by manipulating the instrument manually in a rotating or reciprocating action, or the instrument may be manipulated by attaching the fitting portion 109 of the instrument to a motorized handpiece for effecting more rapid removal of tissue from the root canal, as desired.

Figures 2A, 2B, 2C, 2D, 2E:
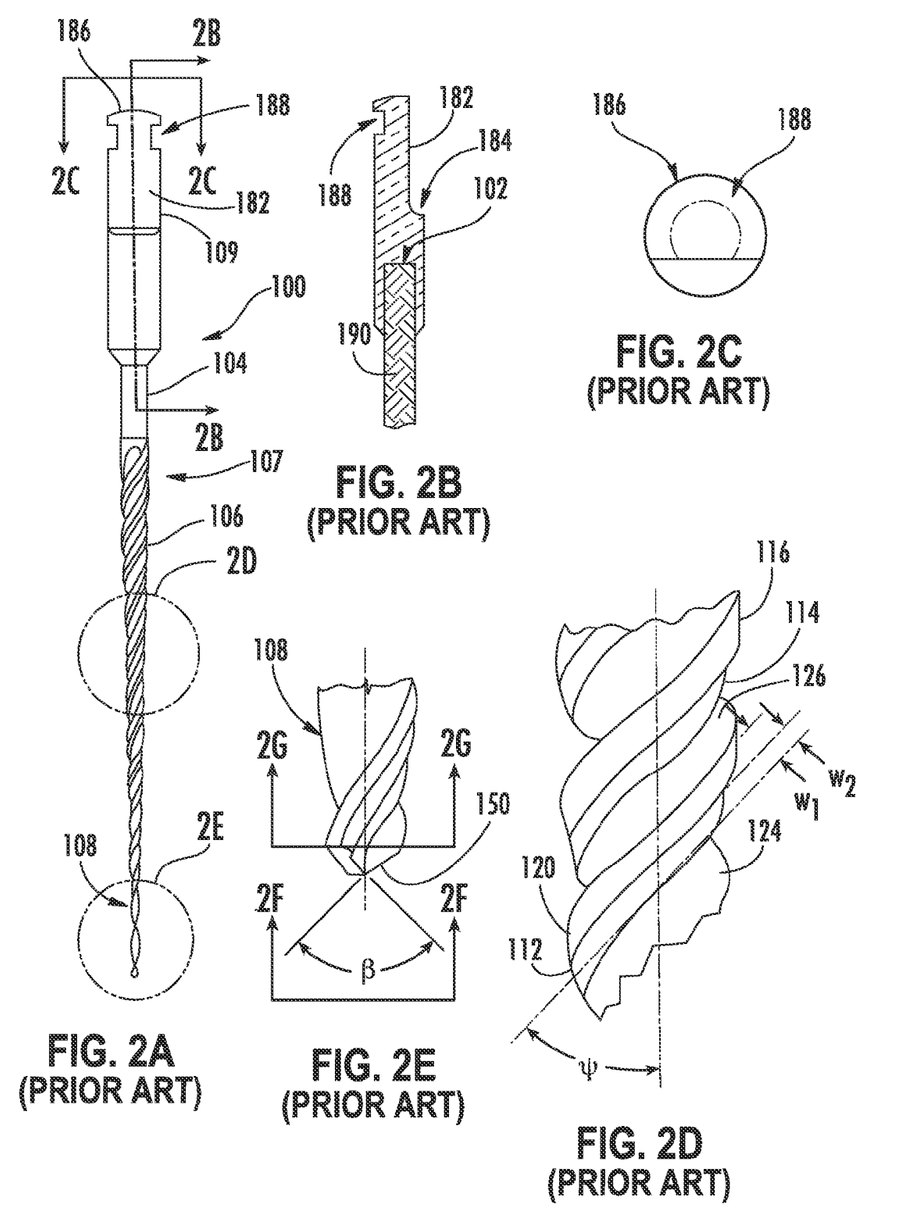
FIGS. 2A-H are various views illustrating a typical prior art fluted endodontic file fabricated from a nickel titanium alloy.

Helical flutes 124 and 126 are typically formed in the working portion 106 extending from the distal end 108 adjacent the tip 150 and exiting at the proximal end 107 (sometimes called the "flute exit" or "exit"), as shown in FIG. 2A. These flutes are typically formed by specialized slow-speed grinding operations using a 3-axis or 6-axis grinding machine in accordance with well-documented manufacturing techniques. Any number of such flutes may be formed in this manner, as desired.

Helical lands 116 and 118 are typically provided generally extending between adjacent flutes 124 and 126. The helical flutes 124, 126 and helical lands 116, 118 intersect one another to define leading edges 128, 132 and trailing edges 130, 134 with respect to clockwise rotation of the instrument (see, e.g. FIG. 2G). The leading edges 128, 132 are typically sharpened to provide a cutting edge for removing tissue from the root canal as the instrument is rotated and/or reciprocated. The trailing edges 130, 134 may be sharpened or not, depending upon the particular file geometries desired and manufacturing conveniences. Rake angles of the cutting edges 128, 132 may be positive, negative, or neutral, depending upon manufacturing convenience and/or clinical purpose. Typical rake angles range from about +20 degrees to about −35 degrees measured with respect to a radial line passing through the cutting edge perpendicular to a line tangent to the periphery of the working portion.

Figures 2F, 2G, 2H:
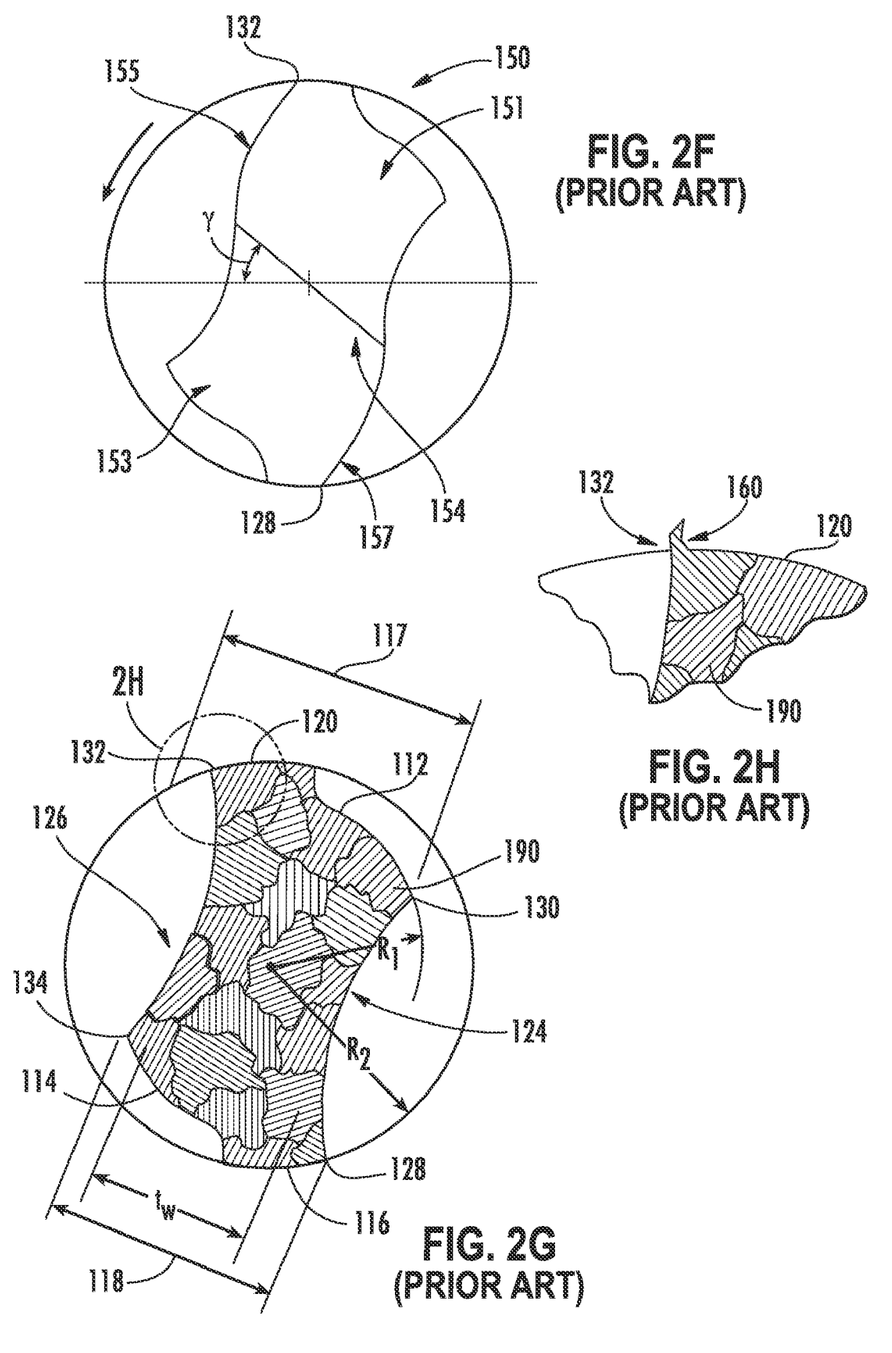

As shown in FIGS. 2D and 2G the helical lands 117, 118 are typically formed so as to define outer peripheral land portions 116, 120 having width $w_1$ (sometimes called the "margin width") and optional recessed land portions 112, 114 having width $w_2$ (sometimes called the "relief width"). The combined width $w_1+w_2$ is sometimes called the "land width." The recessed land portions 112, 114 are at a first predetermined radial distance $R_1$ from the cross-sectional center of the working portion 106. The outer land portions 116, 120 lie at the outer periphery of the working portion 106 at a second predetermined radial distance $R_2$ from the center of the working portion 106, typically about 4 to 30 percent greater than the radial distance $R_1$.

The working portion 106 of the instrument 100 typically has a length ranging from about 3 mm to about 18 mm. A commonly preferred length is about 16 mm. The working portion 106 may have a constant cross-sectional diameter or, more typically, it is tapered from the proximal end 107 to the distal end 108, as shown. In the particular embodiment shown, the taper is substantially uniform—that is, the rate of taper is constant along the working portion 106. A typical taper rate may range from about 0.01 mm/mm to about 0.08 mm/mm. The web thickness "$t_w$"—that is the thickness of the "web" of material between opposed flutes 124, 126—is also typically tapered from the proximal end 107 of the working portion to the distal end 108. The web taper rate is typically between about −0.01 mm/mm to about 0.08 mm/mm.

The tip 150 of the instrument 100 may assume a variety of possible configurations, depending upon the preference of the endodontist and manufacturing conveniences. In the illustrated embodiment, the tip 150 is formed as a chisel edge or chisel tip, as shown in more detail in FIGS. 2E and 2F. The chisel tip 150 generally comprises two or more facets 151, 153 which intersect to define a chisel edge 154. The chisel edge 154 is typically substantially linear and substantially orthogonal to a longitudinal axis of the working portion 106, although such configuration is not necessary. Additional sharpened cutting edges 155, 157 are formed at the tip 150 by the intersection of the facets 151, 153 with the flutes 124, 126. Upon rotation of the instrument in a root canal the chisel edge 154 loosens diseased or decayed tissue while the cutting edges 155, 157 cut and remove the tissue as the file is operated in the canal.

The chisel tip 150 is typically formed by grinding flats or facets 151, 153 into the tip of the instrument 100, as shown, forming the chisel edge 154. The facets 151, 153 define an included point angle $\beta$ typically between about 45-100 degrees, as shown in FIG. 2E. The chisel edge 154 is typically canted from center by a primary angle $\gamma$ of between about 5-25 degrees, as shown in FIG. 2F. As illustrated, The facets 151, 153 of the chisel tip 150 formed apices with the cutting edges 128, 132 and additional cutting edges 155, 157.

The endodontic instrument shown and described in connection with FIG. 2 is formed by grinding away selected portions of material from a tapered rod of a metallic alloy material, such as stainless steel or nickel-titanium ("NiTi"), thereby creating the desired working surface features 116, 118, 124, 126, 128, 130, 132 and 134. The metallic alloy materials presently used, including stainless steel and NiTi, all have crystalline grain structures consisting of a plurality of crystal formations or grains 190 varying in size from about 15 μm to about 200 μm and arranged in a microstructure (see, e.g., FIGS. 2B, 2G & 2F). Such crystalline microstructures are naturally produced by the nucleation and growth of crystalline phases from the molten alloy during cooling and solidification and/or subsequent annealing or other heat processing steps. Essentially, the atoms in the structure arrange themselves in an ordered manner, in which a small repeat unit called a "unit cell" can be identified. This unit cell is repeated in all three directions, and in this way, an ordered crystalline structure is built up.

But crystalline microstructures inherently contain a large number of missing atoms, impurities, and misaligned planes of atoms or dislocations and/or other defects in the arrangement of atoms within the crystalline solid. These defects create material weaknesses which limit the ultimate tensile strength and flexibility of the metal alloy. When exposed on outer surfaces of a formed structure, such defects also tend to create sites prone to stress-induced crack formation, increased friction, material wear and edge degradation.

Crystalline microstructures are also typically malleable and, thus, tend to plastically stretch and/or deform when exposed to large stresses. For example, copper wire is easy to bend because the crystalline micro-structure contains planes of atoms which can slip easily past one another. In the context of cutting tools, the more malleable a material is the more difficult it is to achieve and maintain sharp cutting edges. Thus, the formation of sharp cutting edges in a conventional metal alloy (especially NiTi alloys) is often plagued by the formation of latent burrs, rolled metal deposits and/or other imperfections created along the desired cutting edges by stresses induced during the machining process. This is illustrated in more detail in FIG. 2H. Notably, it may be seen that a burr or rolled metal deposit 160 (not necessarily drawn to scale) extends outward from the cutting edge 132. If such burrs or other similarly occurring imperfections are not carefully monitored and controlled, they can have serious deleterious effects on instrument performance.

FIGS. 3A-H are various views of a fluted endodontic file having features and advantages of the present invention. Except for the modifications discussed below, all other physical and geometric aspects of the instrument 200 are substantially as illustrated and discussed above in connection with FIGS. 2A-H. The file 200 generally comprises a shaft 202 having a shank portion 204 and an elongated working portion 206. The working portion 206 extends from a proximal end 207 adjacent the base of the shank 204 to a distal end 208 terminating in a chisel tip 250. Preferably, the shank portion 204 is integrally formed with or securely gripped by a fitting portion 209 for mating with the chuck of a dental handpiece (see, e.g. FIG. 3B). For this purpose the fitting portion 209 includes a generally I-shaped flat side 282 which defines a step 284 and a generally semicircular disk 286 above and adjacent to a generally semi-circular groove 288. Such fitting 209 is typical of those employed in the dental industry for connecting or interfacing a dental tool with dental drill or handpiece.

Figures 3A, 3B, 3C, 3D, 3E:
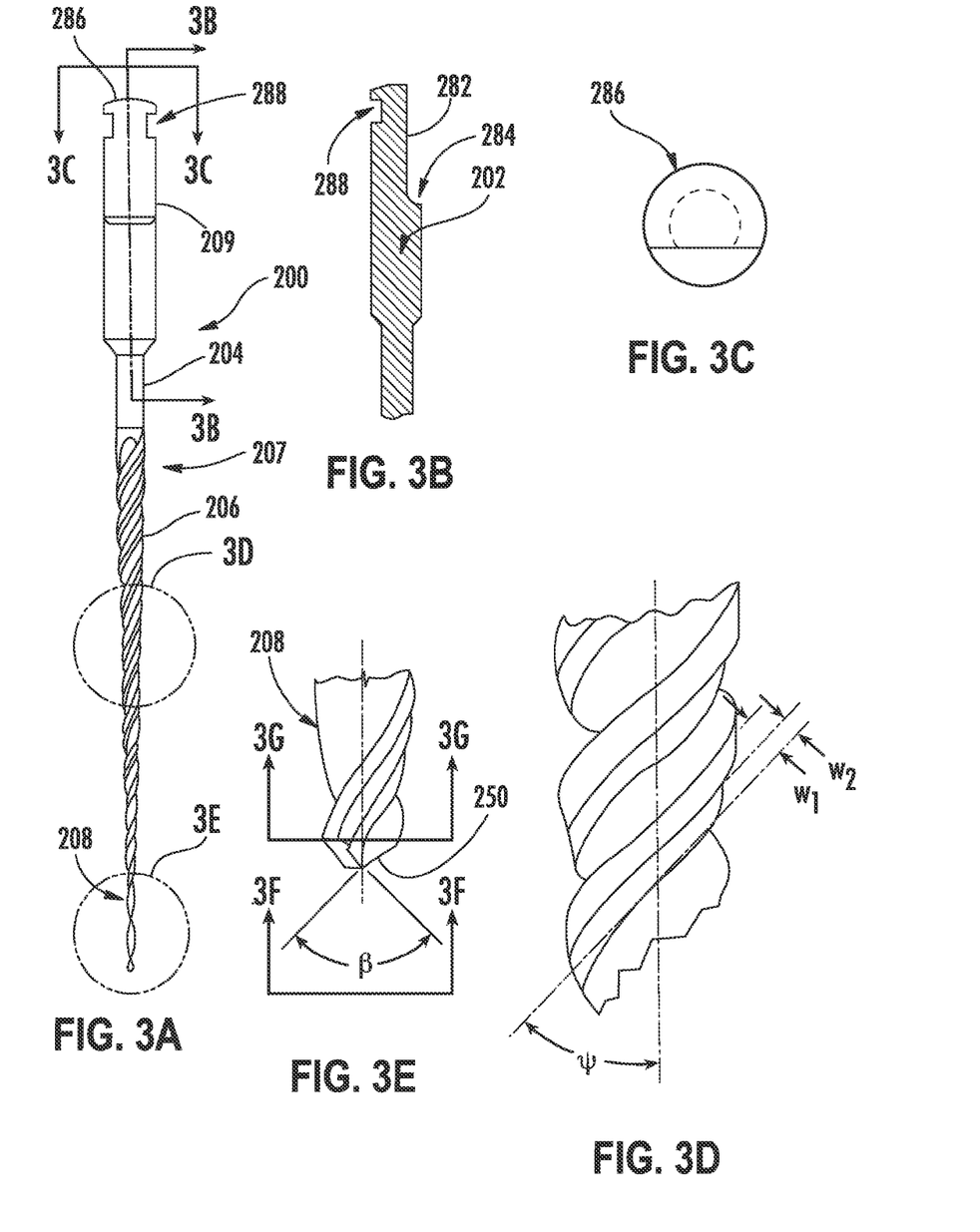
FIGS. 3A-H are various views of one preferred embodiment of an endodontic file having features and advantages in accordance with the present invention.
Figures 3F, 3G, 3H:
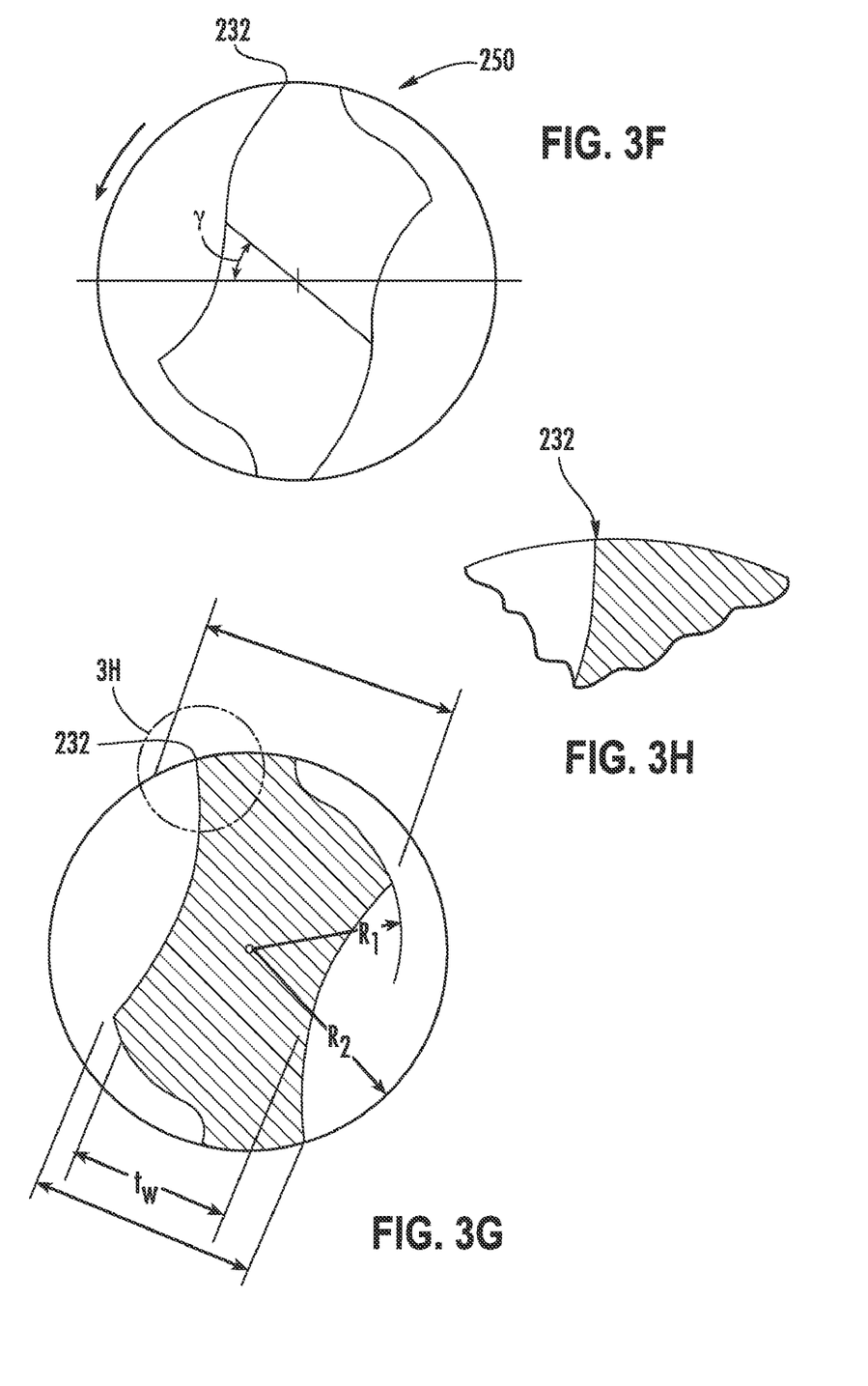

In contrast to the crystalline micro-structure of the instrument 100 illustrated and described above in connection with FIGS. 2A-H, the file 200 is preferably formed substantially entirely of an amorphous or nanocrystalline metal alloy (see, FIGS. 3B, 3F & 3G). Such alloys allow for production of exceedingly durable and wear-resistant endodontic cutting instruments having sharper cutting edges and greater flexibility than conventional steel and NiTi alloys. For purposes of the present description and the appended claims, the term "amorphous" refers to any solid material having no (or essentially no) detectable crystalline structure. The term "nanocrystalline" refers to any solid material having an average crystalline grain size in the nanometer range (or less than about 1 μm).

Figure 4:
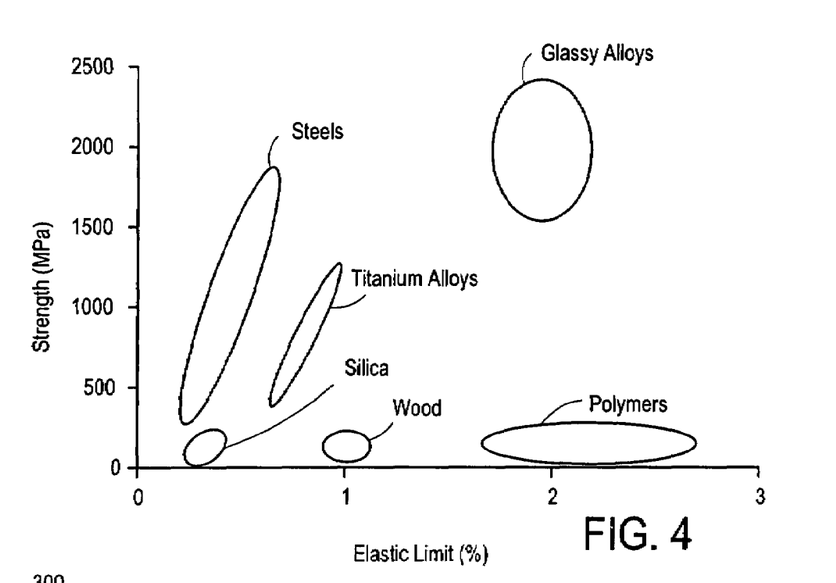
FIG. 4 is a chart illustrating differences in material strength and elasticity among various selected microcrystalline materials and illustrating the superior properties of amorphous metal "glassy" alloys.

Amorphous alloys result from the fact that certain metals, if rapidly cooled, undergo a "glass transition" and can actually freeze as vitreous or semi-vitreous solids. Unlike conventional metals and metal alloys, these "glassy" alloys lack the normal grain boundaries that serve as points of weakness in ordinary crystalline microstructure materials. Such materials possess desirable material properties such as high strength and low modulus of elasticity superior to the limits of conventional microcrystalline materials. Thus, as illustrated by FIG. 4, glassy alloys are typically much stronger than their crystalline metal counterparts (by factors of 2 or 3), are quite tough (much more so than ceramics), and have relatively higher strain limits. These and other desirable properties make amorphous alloys ideally suited for constructing endodontic instruments and similar cutting instruments. Typical physical and mechanical properties are outlined below in TABLE 1.

TABLE 1

| Property | Measured Value (typ.) |
| --- | --- |
| Density ("as cast") | 7.19 (g/cc) |
| Vicker's Hardness | 900 (50 g Load) |
| Tensile Strength | 1.0-1.7 (GPa) |
| Elastic Modulus | 100-110 (GPa) |
| Lamination Factor | >79 (%) |
| Thermal Expansion | 2-7 (ppm/° C.) |
| Crystallization Temperature | 510 (° C.) |
| Continuous Service Temp. | 150 (° C.) |
| Corrosion Resistance | Excellent |
| Wear-Resistance | Excellent |

As noted above, the atoms in an amorphous material are not arranged in any particular pattern or ordered structure. Rather they have a tightly-packed, highly random arrangement. Amorphous materials can be formed by cooling a molten metal alloy quickly enough to prevent crystallization—in other words, fast enough that the atoms do not have time to arrange themselves into an ordered structure. For example, Vitreloy is an amorphous or glassy alloy containing five elements differing dramatically in atomic size and having the approximate elemental composition: 41.2% zirconium, 22.5% beryllium, 13.8% titanium, 12.5% copper, and 10.0% nickel. Because of the varying atomic sizes, and their random arrangement in the vitrified solid, there are no groups of atoms that can easily move past one another. Because there are no planes of atoms in an amorphous material, the atoms are effectively gridlocked into the glassy structure, making the movement of groups of atoms very difficult.

As FIG. 4 illustrates, most conventional solid materials are either: (i) very hard and strong, like steel, but have limited elastic recovery ability; (ii) highly elastic, like plastics and polymers, but have limited hardness and strength; or (iii) a compromise, like titanium, but being superior in neither strength nor elasticity. Advantageously, amorphous alloys, such as Vitreloy, are demonstrably superior in both strength/hardness and elasticity, making such alloys an ideal material for a bendable cutting tool 200. The hardness and relative non-malleability of the material provides for sharp and durable cutting edges 232 and other surface features (FIG. 3H). Cutting edges 232 are easily formed without the aforenoted problem of rolled metal deposits and other defects experienced with grinding or machining of conventional microcrystalline alloy materials. At the same time, the high elastic recovery of the amorphous material allows for a high degree of bending and flexibility, particularly desirable in endodontic applications for accessing and removing hard dentine material deep from within the inner walls of a root canal.

The combination of high strength, hardness and excellent elasticity make Vitreloy and similar amorphous alloys ideal materials for endodontic instruments and similar cutting instruments requiring efficient cutting and removal of dentine and enamel from and within tooth structures and curved root canal surfaces. Other suitable amorphous alloy materials include, without limitation, binary alloy systems including alloys containing zirconium and/or titanium, including NiTi alloys; ternary alloy systems including Cu—Ti—Zr, Ln-Al-TM, Mg-Ln-TM, Zr—Al-TM, Hf—Al-TM and Ti—Zr-TM (wherein Ln is a lanthanide metal, and TM is a transition metal of the Groups VI to VIII); and various other complex alloy systems including Zr—Al—Co—Ni—Cu, Zr—Ti—Al—Ni—Cu, Zr—Ti—Nb—Al—Ni—Cu, and Zr—Ti—Hf—Al—Co—Ni—Cu. Most of these alloy systems (particularly the ternary and more complex alloys) have low critical cooling rates for glass formation and, thus, can be easily produced in bulk shapes with thicknesses of 10-50 mm or more.

In addition to amorphous metal alloys, those skilled in the art will readily appreciate that certain nanocrystalline materials may also find favorable application in the present invention. Nanocrystalline materials have an ultra-fine crystalline grain structure that produces a significantly higher percentage of atoms at grain boundaries. Whereas in conventional polycrystalline materials grain boundaries typically account for less than 1% of the material volume, in nanocrystalline materials they can occupy as much as 50% or more. The predominance of intercrystalline atomic structures at grain boundaries provide marked improvements in material performance and properties very similar to those achieved in the amorphous metal materials described above. However, some nanocrystalline materials can be processed or formed so as to retain certain desired properties of conventional microcrystalline structures, such as malleability and material toughness or energy-absorbing capability. Suitable nanocrystalline materials can be formed in a similar fashion as described above for amorphous metal materials (e.g., by rapid cooling of molten alloy) and/or by the addition of one or more trace elements or impurities selected to provide catalyzing sites for nanocrystalline formation. Preferred nanocrystalline materials have about 5% or greater atoms located at grain boundaries. More preferably at least about 25% of atoms are located at grain boundaries and most preferably at least about 50% to 75% of atoms are located at grain boundaries. A suitable amorphous (or essentially amorphous) material may comprise anywhere from 75% to 100% of atoms located at grain boundaries.

Fabrication of the endodontic instrument 200 may be readily accomplished using any combination of conventional machining and/or grinding techniques well known to those skilled in the art. Thus, the instrument 200 may be fabricated from a round or tapered rod or blank of selected material comprising amorphous metal alloy and/or nanocrystalline alloy material. Because of the relative hardness of the selected material, the formation of sharp cutting edges and other fine or detailed features by conventional grinding operations can be easily achieved at normal grinding speeds and normal-to-high production throughputs. Thus, an improved, high-quality cutting instrument 200 may be reliably manufactured without significantly altering existing manufacturing processes, time or costs.

Alternatively, the instrument 200 may be readily formed at higher production rates by metal injection molding ("MIM") using one or more powdered amorphous or nanocrystalline alloys suspended in a liquid polymer binder. The MIM process is very similar to plastic injection molding and can provide much the same shapes, part geometries and surface features. Very fine metal powder combined with a binder material is injected into a mold. After the binder solidifies, the part is removed from the mold and the part is sintered (solid state diffused) in a controlled atmosphere furnace. The binder is melted or dissolved by the intense heat and vacuum pressure. The part is then further sintered at a controlled temperature and pressure until the powdered metal particles fuse to one another, leaving the resulting part at 94-99% of theoretical density. Subsequent machining operations or processing steps may be employed, as desired, to refine and sharpen cutting edges 232 and/or other surface details as necessary. Advantageously, very high production rates can be achieved through the use of multi-cavity tooling, high-speed injection molding techniques and the like.

Most preferably, the entire instrument 200 is formed as a single, integral molded structure using a modified high-pressure die-casting technique. A selected molten amorphous metal alloy is preferably injected into a die or mold under pressure and is then rapidly cooled or quenched at a rate greater than about 10° C. per second to form the desired solid vitreous metal structure having the desired instrument shape as imparted by the die or mold. Advantageously, it has been discovered that metallic glass alloys can be die-cast in this manner with very high detail and precision as compared to conventional die casting with crystalline metal alloys. For example, Liquidmetal Technologies of Lake Forest, Calif. has developed an amorphous metal alloy material, Liquidmetal™, that can be die-cast with the greatest of precision, for example, down to 1 micron. The solidification of the Liquidmetal alloy exhibits extremely small shrinkage when compared to solidification of ordinary metals. This results largely from the lack of phase transformation in the Liquidmetal alloy from its molten state to its solid state upon cooling and solidification. As such, it is advantageously possible and desirable to die-cast an entire cutting instrument 200 or at least the working portion 207 thereof in virtually whatever intricate or sophisticated design(s) thereof that may be desired (including "as-cast" sharp cutting edges and/or other detailed working surface features) with minimal or no post-finishing processes. Of course, subsequent machining operations or processing steps may be employed, as desired, to deflash, refine and/or hone cutting edges 232 and/or other details as desired. The highest possible manufacturing throughput and efficiency can be achieved through the use of multi-cavity dies, high-speed casting techniques and the like.

Advantageously, such precision die-cast instruments are not only less expensive to manufacture, but the design and physical geometries thereof are not limited by the normal requirements imposed by conventional machining operations. Thus, the manufacturing method in accordance with one embodiment of the invention facilitates the possibility of even more advanced and more sophisticated file geometries, including, for example, multiple tapers, intertwined and/or disjointed flutes and cutting edges, cutting blades, micro-projecting cutting features and/or other desired features in the working surface of an endodontic instrument or similar instrument.

Figure 5A:
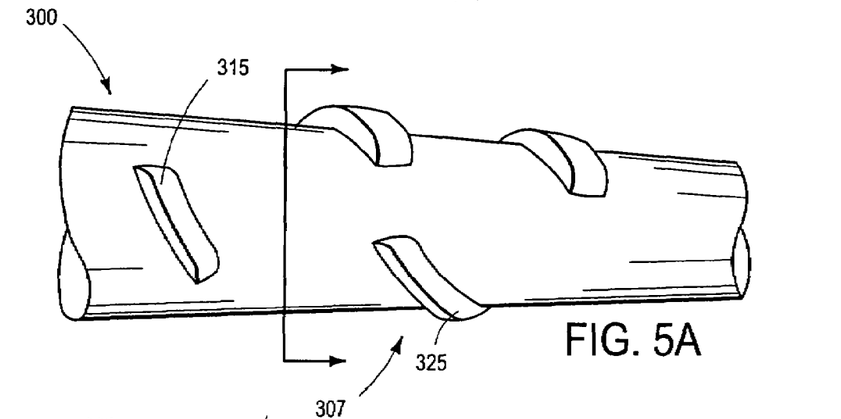
FIGS. 5A-C are various views of a second alternative preferred embodiment of an endodontic file having features and advantages in accordance with the present invention.
Figure 5B:
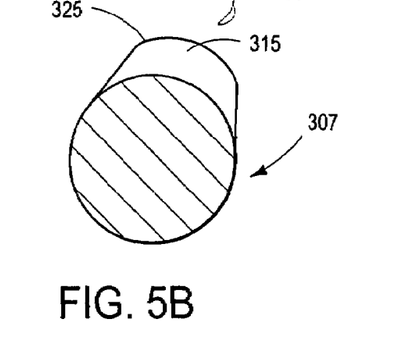
Figure 5C:
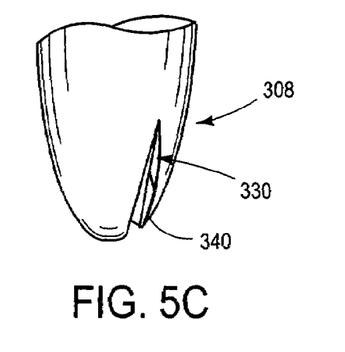

FIG. 5 illustrates one possible embodiment of an advanced endodontic file 300 having features and advantages in accordance with the present invention. The file 300 generally comprises a tapered working portion 307 having multiple projecting cutting blades 315 integrally formed thereon and each having an outer-most exposed cutting edge 325. The entire file structure, including cutting blades 315, sharp cutting edges 325 and other possible desired features (not shown), is preferably die-cast substantially entirely of an amorphous or nanocrystalline metal alloy. The multiple cutting blades 315 preferably are spaced and arranged along the working portion 307 in an irregular, non-symmetric and/or uneven pattern. Preferably, the projecting cutting blades are also formed with different and/or alternating helix angles, rake angles, orientations and projections along substantially the entire length of the working portion 307. Desirably, such cutting blade geometries provide non-continuous, non-uniform cutting edges 325, which, when the instrument is rotated and/or reciprocated within a curved root canal, help promote a continuous canal shape while minimizing the risk of canal penetration. The tip 308 of the instrument 300 preferably is smooth and bullet-shaped, as illustrated in FIG. 5C, with a small notch 330 formed therein, defining at least one sharp cutting edge 340. Of course, those skilled in the art will appreciate that the particular features and geometries described above can be varied to produce additional desired effects without departing from the essential teachings of the invention disclosed herein.

Advantageously, cast endodontic instruments fabricated in accordance with the invention are highly uniform in size and geometry. They have precision formed flutes, cutting edges and other working surface features that are substantially identical with substantially little or no variation from instrument to instrument. Such precision-cast root canal instruments have tremendous clinical advantages and improved efficacy. Furthermore, these instruments reliably perform and behave more predictably and produce more uniform results than can be obtained with presently available machined instruments. It is well known that conventional endodontic instruments vary significantly in flute geometries, taper rates, helix angles, cutting edge orientations and sharpness, and other critical features as a result of normal material sizing variations, machining tolerances and tolerance stacking. Metal injection molding or die casting of endodontic instruments with sharp cutting edges and other working surface features intact eliminate many if not all of these consistency problems.

The concepts and teachings of the present invention are particularly applicable to amorphous alloys and nanocrystalline alloys and endodontic instruments (files, reamers, obturators, drill bits and the like) fabricated therefrom. However, the invention is not limited specifically to endodontic instruments fabricated from the disclosed alloys, but may be practiced with a variety of dental instruments using any one of a number of other suitable alloy materials. Those skilled in the art will also recognize that a variety of well known machining techniques for making conventional endodontic instruments may also generally be applied to the manufacture of instruments as disclosed herein with various known or later developed improvements in materials or processing. For example, suitable instruments may be ground from a straight or tapered rod, twisted, and/or drawn to a taper with or without grinding. Suitable grinding techniques include those described in standard metallurgical texts for grinding various metals. Those skilled in the art will further appreciate that while the particular instruments illustrated and described herein are reamers or files, similar instruments can also be configured for use as condensers or compactors by reversing the direction of twist of the helical flutes and lands and/or reversing the direction of rotation of the instrument.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A method of manufacturing a dental instrument adapted for the shaping and/or removal of tooth structure, said instrument comprising a shaft having a shank portion and a working portion, said working portion having one or more sharp cutting features thereon adapted for the removal of said tooth structure upon rotation and/or reciprocation of the instrument, said method comprising forming the dental instrument by pouring or injecting a metal alloy in a molten or liquid state into a die or mold with a desired instrument shape including said cutting features and then cooling the metal alloy to form an integral as-molded instrument having said one or more sharp cutting features, wherein said cooling step comprises rapidly cooling said alloy from its molten state to a solid state in such a manner that a glassy metal alloy substantially without an ordered crystalline structure is formed.

2. The method of claim 1 wherein said glassy metal alloy comprises one or more of the following elements: zirconium, beryllium, titanium, copper, or nickel.

3. The method of claim 1 wherein said glassy metal alloy comprises one of the following base alloy systems: Zr—Ti, Ni—Ti, Cu—Ti—Zr, Ln-Al-TM, Mg-Ln-TM, Zr—Al-TM, Hf—Al-TM, Ti—Zr-TM, Zr—Al—Co—Ni—Cu, Zr—Ti—Al—Ni—Cu, Zr—Ti—Nb—Al—Ni—Cu, and/or Zr—Ti—Hf—Al—Co—Ni—Cu, where Ln is a lanthanide metal, and TM is a transition metal of the Groups VI to VIII.

4. The method of claim 1 wherein said rapid cooling step is performed at a rate greater than about 10° C. per second to form the desired instrument shape.

5. The method of claim 1, further comprising a machining step to refine the one or more sharp cutting features.

* * * * *